United States Patent [19]

Weller, III et al.

[11] Patent Number: 4,849,525
[45] Date of Patent: Jul. 18, 1989

[54] PHOSPHINYLCYCLOALKYLCARBONYL AND PHOSPHINYLCYCLOALKENYLCARBONYL DIPEPTIDES

[75] Inventors: Harold N. Weller, III; Eric M. Gordon, both of Pennington, N.J.

[73] Assignee: E. R. Squibb & Sons, Inc., Princeton, N.J.

[21] Appl. No.: 98,651

[22] Filed: Sep. 21, 1987

[51] Int. Cl.$^4$ .............................................. C07D 207/00
[52] U.S. Cl. ...................................... 548/413; 548/112
[58] Field of Search ............... 548/336, 413, 406, 112; 514/63, 91; 546/22; 540/542

[56] References Cited

U.S. PATENT DOCUMENTS

| 4,374,131 | 2/1983 | Petrillo, Jr. | 424/200 |
| 4,381,287 | 4/1983 | Karanewsky et al. | 424/200 |
| 4,384,123 | 5/1983 | Petrillo, Jr. | 548/409 |
| 4,432,971 | 2/1984 | Karanewsky et al. | 424/177 |
| 4,468,519 | 8/1984 | Krapcho | 548/409 |
| 4,499,079 | 2/1985 | Weller et al. | 514/2 |
| 4,560,506 | 12/1985 | Weller et al. | 260/112.5 |
| 4,560,681 | 12/1985 | Karanewsky | 514/82 |

OTHER PUBLICATIONS

Weller et al., Biochemical and Biophysical Research Communications; Design of Conformationally Constrained Angiotensin-Converting Enzyme Inhibitors, Nov. 30, 1984, vol. 125, pp. 82–89.

*Primary Examiner*—Mary C. Lee
*Assistant Examiner*—E. Brendan Magrab
*Attorney, Agent, or Firm*—Donald J. Barrack; Stephen Venetianer

[57] ABSTRACT

Compounds of the formula

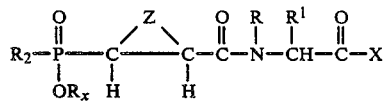

and their pharmaceutically acceptable salts wherein Z completes a cycloalkyl ring, a substituted cycloalkyl ring, a cycloalkenyl ring, a substituted cycloalkenyl ring or a saturated heteroalkyl ring; $R_2$ is lower alkyl, aralkyl or aminoalkyl and X is an amino or imino acid. The compounds possess angiotensin converting enzyme inhibition activity.

10 Claims, No Drawings

PHOSPHINYLCYCLOALKYLCARBONYL AND PHOSPHINYLCYCLOALKENYLCARBONYL DIPEPTIDES

BACKGROUND OF THE INVENTION

U.S. Pat. No. 4,560,506 discloses mercaptocycloalkyl-carbonyl and mercaptoarylcarbonyl dipeptide compounds having angiotensin converting enzyme inhibition activity and enkephalinase inhibition activity.

U.S. Pat. No. 4,499,079 discloses carboxy and substituted carboxy alkanoyl and cycloalkanoyl peptides compounds having angiotension converting enzyme inhibition activity.

SUMMARY OF THE INVENTION

This invention is directed to the phosphinylcycloalkylcarbonyl and phosphinylcycloalkenylcarbonyl compounds of formula I and pharmaceutically acceptable salts thereof (I)

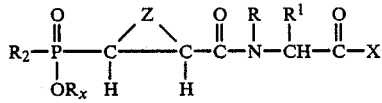

wherein Z completes a cycloalkyl ring of 3 to 10 carbon atoms; a cycloalkyl ring of 3 to 10 carbon atoms in which one of the carbon atoms is substituted by a lower alkyl of one to four carbon atoms, a lower alkoxy of one to four carbon atoms, a lower alkylthio of one to four carbon atoms, a phenyl, benzyl, halo, trifluoromethyl or hydroxy group; a cycloalkenyl ring of five to seven carbon atoms or a heteroalkyl ring of five to seven atoms wherein the hetero ring contains an oxygen, sulfur or nitrogen.

X is an amino or imino acid of the formula

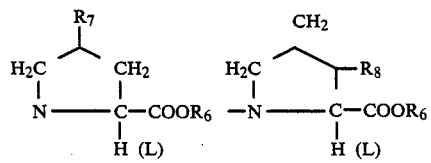

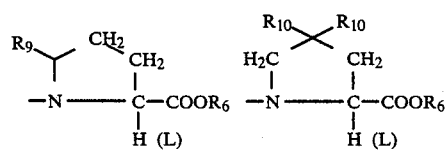

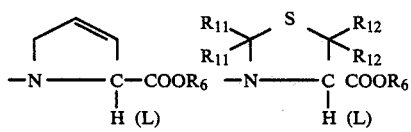

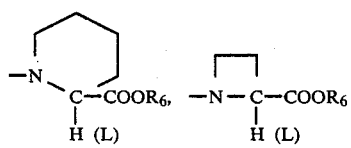

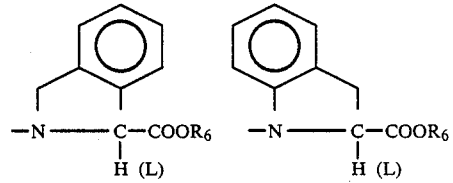

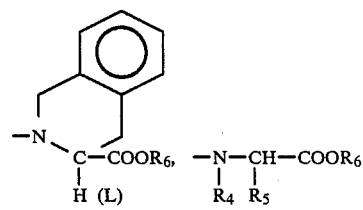

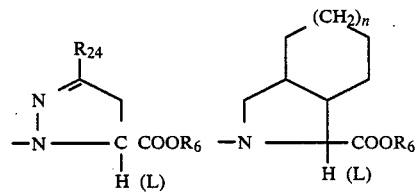

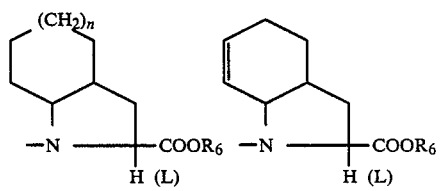

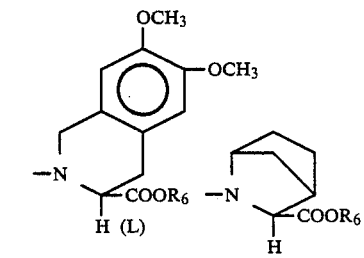

n is zero, one or two.

$R_{25}$ is lower alkyl of 1 to 4 carbons or $-(CH_2)_r-$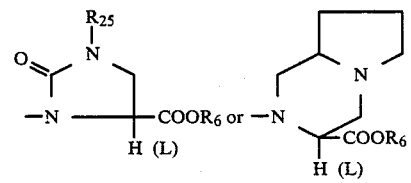

$R_7$ is hydrogen, lower alkyl, halogen, hydroxy, $-NH-\overset{O}{\overset{\|}{C}}-$lower alkyl, amino, $-N\overset{R_{19}}{\underset{R_{20}}{\diagdown}}$

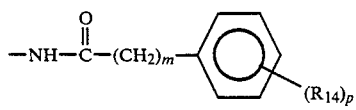

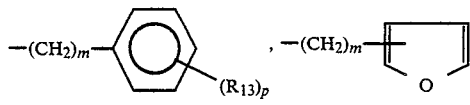

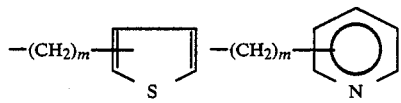

a 1- or 2-naphthyl of the formula

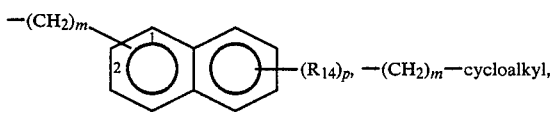

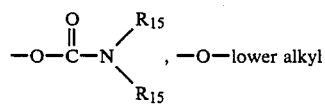

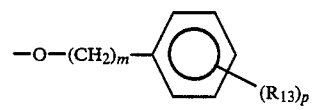

a 1- or 2-naphthyloxy of the formula

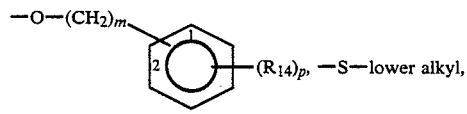

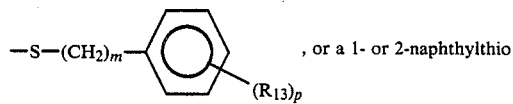

$R_8$ is halogen,

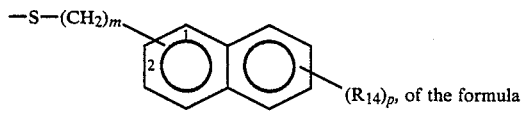

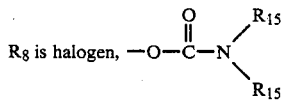, lower alkyl, a 1- or 2-naphthyloxy of the formula

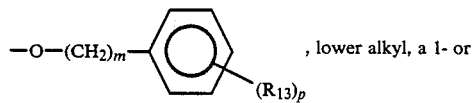

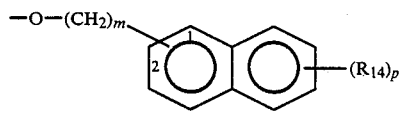

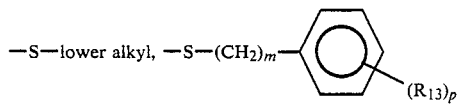

or a 1- 2-naphthylthio of the formula

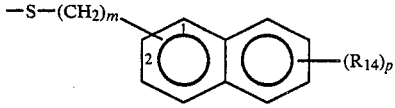

$R_9$ is keto or 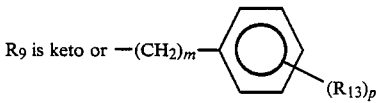

$R_{10}$ is halogen or $-Y-R_{16}$.

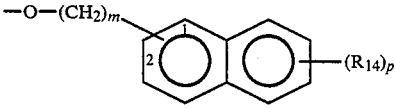

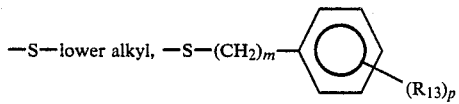

or a 1- 2-naphthylthio of the formula

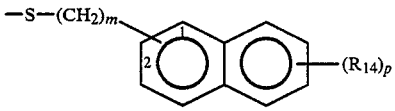

$R_9$ is keto or 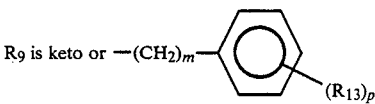

$R_{10}$ is halogen or $-Y-R_{16}$.

$R_{11}$, $R'_{11}$, $R_{12}$ and $R'_{12}$ are independently selected from hydrogen and lower alkyl or $R'_{11}$, $R_{12}$ and $R'_{12}$ are hydrogen and $R_{11}$ is

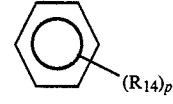

$R_{13}$ is hydrogen, lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl.

$R_{14}$ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy.

m is zero, one, two, three or four.

p is one, two or three provided that p is more than one only if $R_{13}$ or $R_{14}$ is hydrogen, methyl, methoxy, chloro, or fluoro.

$R_{15}$ is hydrogen or lower alkyl of 1 to 4 carbons.

Y is oxygen or sulfur
R$_{16}$ is lower alkyl of 1 to 4 carbons,

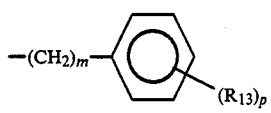

or the R$_{16}$ groups join to complete an unsubstituted 5- or 6-membered ring or said ring in which one or more of the carbons has a lower alkyl of 1 to 4 carbons or a di(lower alkyl of 1 to 4 carbons) substituent.

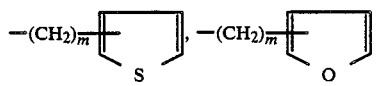

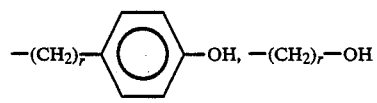

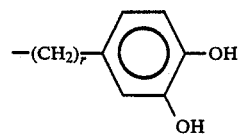

R$_5$ is hydrogen, lower alkyl 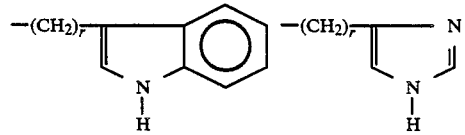

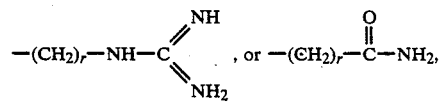

—(CH$_2$)$_r$—NH$_2$, —(CH$_2$)$_r$—SH, —(CH$_2$)$_r$—S—lower alkyl.

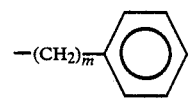, or —(CH$_2$)$_r$—C—NH$_2$, r is an integer from 1 to 4.
R$_{19}$ is lower alkyl, benzyl, or phenethyl.
R$_{20}$ is hydrogen, lower alkyl, benzyl or phenethyl.
R is hydrogen, lower alkyl, cycloalkyl, —(CH$_2$)$_2$—NH$_2$, —(CH$_2$)$_3$—NH$_2$, —(CH$_2$)$_4$—NH$_2$,
—(CH$_2$)$_2$—OH, —(CH$_2$)$_3$—OH, —(CH$_2$)$_4$—OH,
—(CH$_2$)$_2$—SH, —(CH$_2$)$_3$—SH, or —(CH$_2$)$_4$—SH.

R$_1$ is hydrogen, lower alkyl, halo substituted lower alkyl,

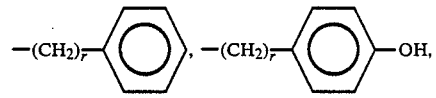

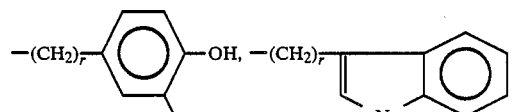

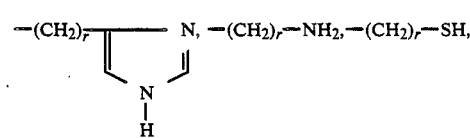

—(CH$_2$)$_r$—OH, —(CH$_2$)$_r$—S—lower alkyl,

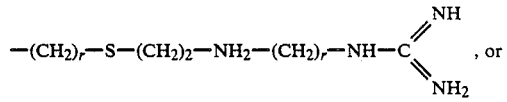

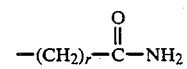

R$_2$ is lower alkyl, aralkyl or aminoalkyl.
R$_6$ and R$_x$ are hydrogen, lower alkyl, benzyl, benzyhydryl, a pharmaceutically acceptable salt ion

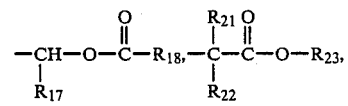

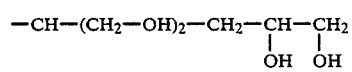

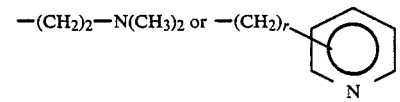

R$_{17}$ is hydrogen, lower alkyl, cycloalkyl, or phenyl.
R$_{18}$ is hydrogen, lower alkyl, lower alkoxy or phenyl or
R$_{17}$ and R$_{18}$ taken together are —(CH$_2$)$_2$—, —CH$_2$)$_3$—, —CH=CH—, or

$R_{21}$ and $R_{22}$ are independently selected from hydrogen and lower alkyl.

$R_{23}$ is lower alkyl.

$R_{24}$ is hydrogen, lower alkyl,

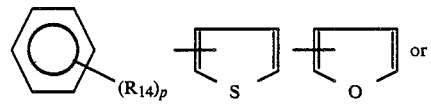

q is zero or one.

DETAILED DESCRIPTION OF THE INVENTION

This invention in its broadest aspects relates to the dipeptide compounds of formula I above, to compositions and the method of using such compounds as pharmaceutical agents.

The term lower alkyl used in defining various symbols refers to straight or branched chain radicals having up to seven carbons. The preferred lower alkyl groups are up to four carbons with methyl and ethyl most preferred. Similarly the terms lower alkoxy and lower alkylthio refer to such lower alkyl group attached to an oxygen sulfur.

The term cycloalkyl refers to saturated rings of 3 to 10 carbon atoms with cyclopentyl, cyclohexyl, and cycloheptyl being most preferred.

The term halo substituted lower alkyl refers to such lower alkyl groups described above in which one or more hydrogens have been replaced by chloro, bromo, or fluoro groups such as trifluoromethyl, which is preferred, pentafluoroethyl, 2,2,2-trichloroethyl, chloromethyl, bromomethyl, etc.

The term aralkyl as used herein refers to lower alkyl groups as discussed above having an aryl or substituted aryl substituent.

The term aminoalkyl as used herein refers to lower alkyl groups as discussed above having an amino or substituted amino substituent.

The symbols

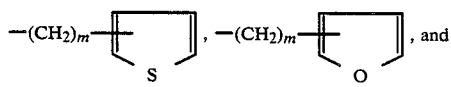

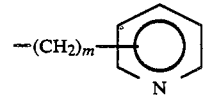

represent that the alkylene bridge is attached to an available carbon atom.

The compounds of formula I wherein Z completes an unsubstituted cyclohexyl ring, $R_2$ is aralkyl, R is hydrogen, $R_1$ is methyl and X is proline are prepared by reacting a compound of the formula

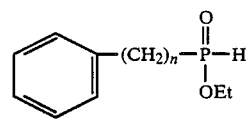

II dissolved in an organic solvent wherein n is an integer from one to eight with trimethylsilylchloride and triethylamine. The resulting mixture is reacted with methyl α-chloroacrylate to yield a compound of the formula

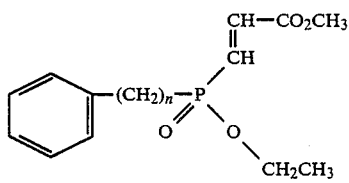

III

The compounds represented by formula III are reacted with butadiene to form compounds of the formula

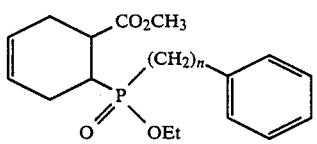

IV

The ester groups of formula IV are removed by treatment with strong base followed by strong acid to yield compounds of the formula

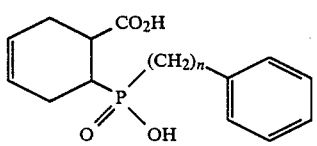

V

The compounds of formula V are dissolved in an organic solvent such as tetrahydrofuran to which carbonyldiimidazole is added. The resulting mixture is reacted with L-alanyl-L-proline benzyl ester tosylate to yield a compound of the formula

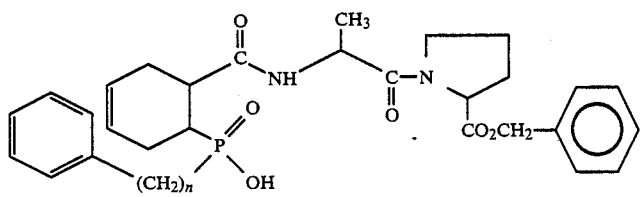

VI

The compounds of formula VI are hydrogenated and the appropriate salt is isolated after reaction with a base supplying the desired ion as represented by formula VII

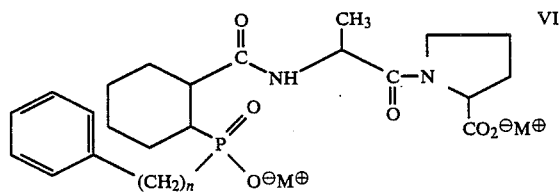

VII wherein M is a sodium, or lithium, potassium, calcium or magnesium.

Substituted cyclohexyl compounds may be prepared by starting with the appropriately substituted butadiene to form a compound of formula IV and then following the above-described synthesis. Cyclohexenyl compounds can be prepared by modifying the deprotection step described above. For example, removal of the benzyl ester group by saponification with sodium hydroxide leaves the double bond of the cyclohexyl ring in formula VI intact. The $R_1$ and X substituents of formula I can be varied by using the appropriate dipeptide in place of alanyl proline benzyl ester to react with formula V.

The compounds of formula I where Z completes a ring other than cyclohexyl and where Z completes a heteroalkyl ring are prepared in a similar manner as described above except the following compound

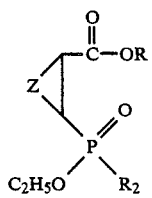

VIII is substituted for the compound of formula IV. The compounds of formula VIII are prepared by reacting a compound of the formula

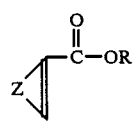

IX wherein R is hydrogen or lower alkyl with a compound of the formula

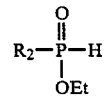

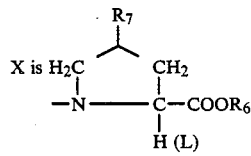

X

The reaction between compounds IX and X is analogous to the reaction described in an article by J. K. Thottehil et. al., Tetrahedran Letters, Vol. 25, pp. 4741–4744 (1984). The compound of formula VIII is then treated in the same manner as the compounds of formula IV to yield corresponding compounds of formula I.

Preferred compounds of this invention with respect to the peptide part of the structure of formula I are those wherein:

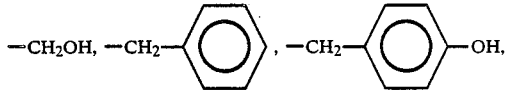

$R_1$ and $R_9$ are independently selected from hydrogen, straight or branched chain lower alkyl of 1 to 4 carbons,

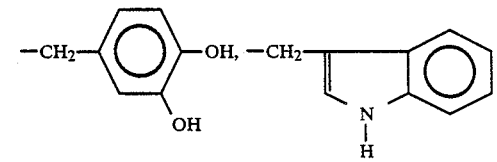

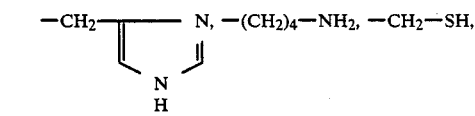

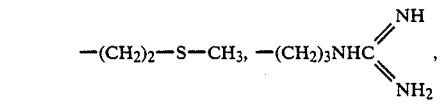

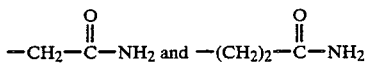

R₇ is hydrogen, cyclohexyl, lower alkoxy or 1 to 4 carbons,

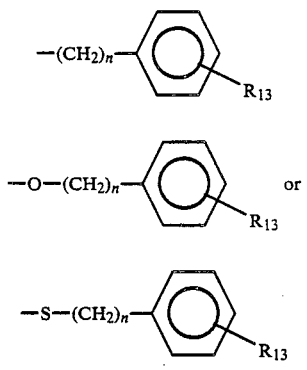

wherein n is zero, one or two and R₁₃ is hydrogen, methyl, methoxy, methylthio, Cl, Br, F, or hydroxy.

t is two or three.

R₆ is hydrogen, an alkali metal salt, straight or branched chain alkyl of 1 to 4 carbons, or

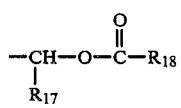

R₁₇ is hydrogen, straight or branched chain lower alkyl of 1 to 4 carbons, cyclohexyl and R₁₈ is straight or branched chain lower alkyl of 1 to 4 carbons or phenyl.

R₈ is hydrogen or cycloalkyl of 5 to 7 carbons.

Most preferred compounds of this invention with respect to the peptide part of the structure of formula I are those having the structure

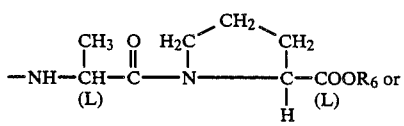

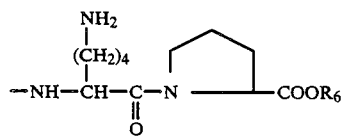

wherein R₆ is hydrogen, ethyl,

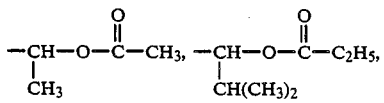

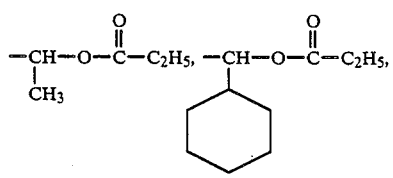

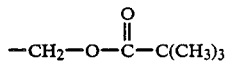

or an alkali metal salt.

Preferred compounds of this invention with respect to Z is where Z completes a cycloalkyl ring of 4 to 7 carbons, a cycloalkyl ring of 4 to 7 carbons wherein one of the carbons is substituted by a methyl, methoxy, methylthio, Cl, Br, F, or hydroxy, or a cyclohexenyl ring.

The compounds of formula I wherein R₆ is hydrogen form salts with a variety of inorganic or organic bases. The nontoxic, pharmaceutically acceptable salts are preferred, although other salts are also useful in isolating or purifying the product. Such pharmaceutically acceptable salts include alkali metal salts such as sodium, potassium or lithium, alkaline earth metal salts such as calcium or magnesium and salts derived from amino acids such as arginine, lysine, etc. The salts are obtained by reacting the acid form of the compound with an equivalent of the base supplying the desired ion in a medium in which the salt precipitates or in aqueous medium and then lyophilizing.

The peptide portion of the molecule of formula I when R₁ is other than hydrogen contains an asymmetric center. Preferably, this center will be in the L-configuration. The side chain containing the moiety gives rise to cis-trans isomerism.

Thus the compounds of formula I can exist in diastereoisomeric forms or in mixtures thereof. The above described processes can utilize racemates, enantiomers or diastereomers as starting materials. When diastereomeric products are prepared, they can be separated by conventional chromatographic or fractional crystallization methods.

The products of formula I wherein the imino acid ring (X) is monosubstituted also give rise to cis-trans isomerism. The configuration of the final product will depend upon the configuration of the R₇, R₈ and R₉ substituent in the starting material of the compound reacted with formula V.

The compounds of formula I, and the pharmaceutically acceptable salts thereof, are hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensinogen (renin) angiotensin I (ACE) angiotensin II sequence by inhibiting angiotensin converting enzyme and reducing or eliminating the formation of the pressor substance angiotensin II. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg., preferably about 1 to 50 mg, per kg. of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 500 mg., preferably about 30 to 330 mg of a compound of this invention, and about 15 to 300 mg, preferably about 15 to 200 mg of the diuretic, to a mammalian species in need thereof. Exemplary of the diuretics contemplated for use in combination with a compound of this invention are the thiazide diuretics, e.g., chlorothiazide, hydrochlorothiazide, flumethiazide, hydroflumethiazide, bendroflumethiazide, methyclothiazide, trichloromethiazide, polythiazide, methylclothiazide, tri chloromethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, or in sterile solution or suspension for parenteral administration. About 10 to 500 mg of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples are illustrative of the invention. Temperatures are given in degrees centigrade.

EXAMPLE 1

(trans)-1-[N-[[2-[Hydroxy(4-phenylbutyl)phosphinyl]-cyclohexyl]carbonyl]-L-alanyl]-L-proline, isomer A, dilithium salt

EXAMPLE 1A (E)-3-[Ethoxy(4-phenylbutyl)phosphinyl]-2-propenoic acid, methyl ester A solution of (4-phenylbutyl)-phosphinic acid, ethyl ester (8.0 g, 35.4 mmols) in chloroform (40 ml) were added trimethylsilyl chloride (13.5 ml, 106 mmols) and triethylamine (19.7 ml, 142 mmols). The resulting mixture was stirred at 25° C. for 2.5 hours, after which it was concentrated in vacuo. To the residue were added methyl α-chloro=acrylate (20 g, 0.16 mole, prepared as described by C. S. Marvel and J. C. Cowan, *J. Amer. Chem. Soc.* 61, 3156 (1939)) and triethylamine (9.0 ml, 64 mmol). The resulting yellow mixture was stirred overnight at 65° C., resulting in an orange semisolid. The mixture was diluted with ethyl acetate and washed sequentially with 1N hydrochloric acid and saturated sodium bicarbonate solution, dried (MgSO4), and concentrated to an orange oil. The oil was chromotographed on LPS-1 silica gel, eluting with a gradient from 1:1 hexane:ethyl acetate to ethyl acetate, to give the title compound.

Microanalysis: Calculated for $C_{16}H_{23}O_4P\cdot 0.4H_2O$: C=60.50, H=7.55, P=9.75;
Found C=60.50, H=7.38, P=9.4.

EXAMPLE 1B trans-6-[ethoxy(4-phenylbutyl)phosphinyl]-3-cyclohexene-1-carboxylic acid, methyl ester A solution of the title compound from Example 1A (3.72 g, 12.0 mmols) in a minimum amount of toluene (ca 5 ml) was transferred to a 25×150 mm glass tube which served as a liner of a stainless steel Parr pressure bomb. The bomb and its contained tube were cooled to −78° C. and a stream of butadiene was bubbled through the mixture until the glass tube was nearly full. The pressure bomb was then quickly sealed and allowed to warm to room temperature. The bomb and its contents were then heated to 100° C. and maintained at that temperature for 24 hours, after which they were cooled to room temperature. The pressure was released from the bomb and methanol was added to the contents, resulting in a gelatinous precipitate. The precipitate was removed by filtration and the filtrate was concentrated to a clear oil (3.52 g) The oil was chromatographed on LPS-1 silica gel, eluting with ethyl acetate, to give the title compound (2.6 g, 59%, $R_f$ 0.2).

EXAMPLE 1C trans-6-[hydroxy(4-phenylbutyl)phosphinyl]-3-cyclohexene-1-carboxylic acid A mixture of the title compound of Example 1B (1.4 g, 3.85 mmols), 1N sodium hydroxide solution (4.0 ml, 4.0 mmols), and methanol (4.0 ml) was stirred at 100° C. for 24 hours, after which it was diluted with water. The mixture was acidified by addition of hydrochloric acid and extraction with ethyl acetate. The extract was dried (MgSO4) and concentrated to give a glassy oil (1.1 g). HPLC analysis of the residue (90% aqueous methanol containing 0.2% phosphoric acid eluant on a Whatman ODS-2 analytical column with UV detection at 220 nm) showed three major components of retention times 3.5, 4.0 and 4.8 minutes, respectively, and in a ratio of 27:53:17. The title compound was isolated as the major component ($R_t$ 4.0 min) by preparative HPLC (Whatman ODS-2 "Magnum 20" preparative column eluting with 80% aqueous methanol containing 0.05% trifluoroacetic acid). The yield was 850 mg (69%).

Microanalysis: Calculated for $C_{17}H_{23}O_4P\cdot 0.25H_2O$: C=62.49, H=7.25, P=9.48.
Found: C=62.49, H=7.29, P=9.1.

EXAMPLE 1D trans-1-[N-[[6-hydroxy(4-phenylbutyl)phosphinyl-3-cyclohexen-1-yl]-L-alanyl-L-proline, benzyl ester Isomers A and B To a solution of the title compound of Example 1C (550 mg, 1.71 mmol) in THF (5 ml) at 25° C. was added carbonyldiimidazole (450 mg, 2.7 mmol). The resulting mixture was stirred at 25° L C. for 1 hour, after which L-alanyl-L-proline benzyl ester tosylate salt (1.21 g, 2.7 mmol) and triethylamine (400 μl, 2.8 mmol) were added. The resulting mixture was stirred at 25° C. for 18 hours, after which it was poured into excess 1N hydrochloric acid. The mixture was extracted with ethyl acetate (3x); the extract was dried (MgSO4) and concentrated to give a colorless glass (1.13 g). HPLC analysis (YMC A-302 ODS column, 4.6×150 mm, eluting with 1.0 ml/min of 78% aqueous methanol containing 0.2% phosphoric acid, UV monitoring at 220 nm) showed two major products ($R_t$=6.03 and 6.60 min) in a ratio of 1:1. The products were separated by preparative HPLC (YMC S-15 ODS column, 20×500 mm, eluting with 22 ml/min of 80% aqueous methanol containing 0.5% trifluoroacetic acid, retention times 12.8 min and 14.8 min, respectively) to give trans-1-[N-[[6-hydroxy(4-phenylbutyl)phosphinyl-3-cyclohexen-1-yl]-L-alanyl-L-proline, benzyl ester Isomer A (420 mg, 42%, analytical $R_t$=6.04 min) and trans-1-[N-[[6-hydroxy(4-phenylbutyl)phosphinyl-3-cyclohexen-1-yl]-L-alanyl-L-proline, benzyl ester Isomer B (360 mg, 36%, analytical $R_t$=6.57 min).

EXAMPLE 1E trans-1-[N[[6-hydroxy(4-phenylbutyl)phosphinyl-3-cyclohexen-1-yl]carbonyl]-L-alanyl-L-alanyl-L-proline, dilithium salt, Isomer A A mixture of trans-1-[N-[[6-hydroxy(4-phenyl-butyl)phosphinyl-3-cyclohexen-1-yl]-L-alanyl-L-proline, benzyl ester Isomer A (420 mg, 0.72 mmol) and palladium hydroxide (100 mg of 20% carbon) in methanol (10 ml) was hydrogenated at 25° C. and one atmosphere for 48 hours, after which it was filtered and concentrated to give a glassy residue (245 mg). HPLC analysis of the residue (YMC A302 ODS column, 1.0 ml/min of 70% aqueous methanol containing 0.2% phosphoric acid, UV monitoring at 220 nM) indicated the presence of one major product ($R_t$ 6.3 min) along with several minor contaminants. The major product was isolated by preparative HPLC (YMC S-15 ODS column, 20×500 mm, eluting with 75% aqueous methanol containing 0.1% trifluoroacetic acid) to give a colorless glass (180 mg 49%). Spectroscopic analysis ($^{13}$C and $^1$H NMR, Mass spec) indicated that the product was the corresponding methyl ester resulting from exchange of the benzyl ester with methanol. This material was dissolved in methanol (0.7 ml) and 1.0N lithium hydroxide solution was added (0.7 ml). The mixture was stirred at 25° C. for 31 hours after which it was diluted with water and washed with ether (discard wash). The pH of the aqueous solution was adjusted to approximately 6.0 by addition of AG-50 ion exchange resin; the mixture was filtered and lyophilized to give a fluffy white solid. This material was chromatographed on HP-20, eluting with a water to methanol gradient. Fractions were monitored by HPLC (as above, RT=4.88 min); those containing the desired product were combined and concentrated. The residue was dissolved in water and lyophilized to give the title compound (50 mg, 15%) as a fluffy white solid.

Microanalysis: calculated for $C_{25}H_{35}N_2O_6P\cdot 2Li$; 4.0H$_2$O C=52.09, H=7.52, N=4.86 P=5.37.

Found C=52.27, H=7.51, N=4.83, P=4.47.

M.P>225° C.

EXAMPLE 2

(trans)-1-[N-[[2-[Hydroxy(4-phenylbutyl)phosphinyl]cyclohexyl]carbonyl]-L-alanyl]-L-proline, isomer B, dilithium salt A mixture of trans-1-[N-[[6-hydroxy(4-phenylbutyl)-phosphinyl-3-cyclohexene-1-yl]-L-alanyl-L-proline, benzyl ester Isomer B (360 mg, 0.62 mmol) and palladium hydroxide (100 mg of 20% on carbon) in ethyl acetate (10 ml) was hydrogenated at one atmosphere and 25° C. for 21 hours, after which it was filtered and concentrated. The residue was dissolved in water and 1N lithium hydroxide solution (1.2 ml) was added. The mixture was applied to a column of HP-20 and eluted with a water to methanol gradient. Fractions were monitored by HPLC (YMC A302 ODS column, 1.0 ml/min of 70% aqueous methanol containing 0.2% phosphoric acid, UV monitoring at 220 nm); those containing the major product (T$_t$ 5.3 min) were combined and concentrated. The residue was dissolved in water, charcoal filtered, and lyophilized to give the title compound as a fluffy white solid.

Microanalysis calculated for $C_{25}H_{35}N_2O_6P\cdot 2Li$; 2.7H$_2$O C=54.29, H=7.36, IV=5.07 P=5.60.

Found C=54.27, H=7.49, N=5.04, P=5.26.

M.P>225° C.

What is claimed is:

1. A compound of the formula

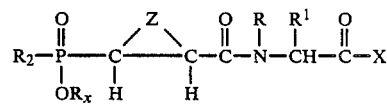

wherein Z completes a cycloalkyl ring of 3 to 10 carbon atoms; a cycloalkyl ring of 3 to 10 carbon atoms in which one of the carbon atoms is substituted by a lower alkyl of one to four carbon atoms, a lower alkoxy of one to four carbon atoms, a lower alkylthio of one to four carbon atoms, a phenyl, benzyl, halo, trifluoromethyl or hydroxy group; a cycloalkenyl ring of five to seven carbon atoms; X is

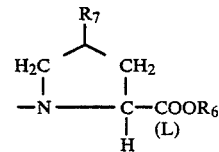

$R_7$ is hydrogen, cyclohexyl, lower alkoxy of 1 to 4 carbons,

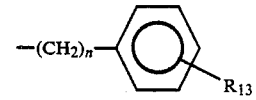

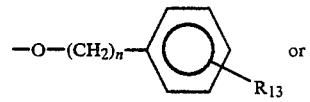

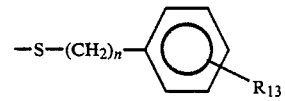

wherein n is zero, one or two and $R_{13}$ is hydrogen, methyl, methoxy, methylthio, Cl, Br, F, or hydroxy.

$R_6$ and $R_x$ are hydrogen, an alkali metal salt straight or branched chain alkyl of 1 to 4 carbons, or

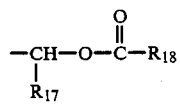

R₁₇ is hydrogen, straight or branched chain lower alkyl of 1 to 4 carbons, cyclohexyl and R₁₈ is straight or branched chain lower alkyl of 1 to 4 carbons or phenyl;

R is hydrogen, lower alkyl, cycloalkyl,

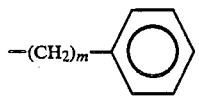 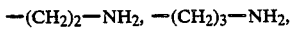

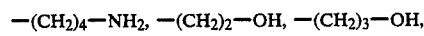

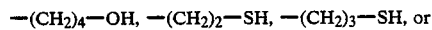

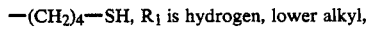, R₁ is hydrogen, lower alkyl, halo substituted lower alkyl, ,

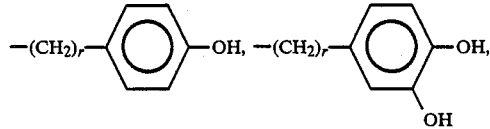

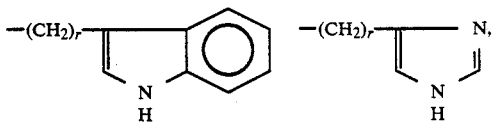

—(CH₂)ᵣ—NH₂, —(CH₂)ᵣ—SH, —(CH₂)ᵣ—OH,

—(CH₂)ᵣ—S—lower alkyl,

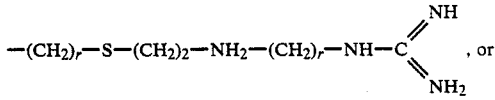

$$-(CH_2)_r-\overset{O}{\overset{\|}{C}}-NH_2;$$

Y is an integer from 1 to 4;

R₂ is lower alkyl, phenylalkyl, or aminoalkyl.

2. A compound according to claim 1 wherein Z completes a cycloalkyl ring.

3. A compound according to claim 2 wherein Z completes a cyclohexyl ring.

4. A compound according to claim 1 wherein R₇ is hydrogen and R₆ is hydrogen or an alkali metal salt.

5. A compound according to claim 1 wherein R₂ is phenylalkyl.

6. A compound according to claim 1 wherein R is hydrogen.

7. A compound according to claim 1 wherein R¹ is lower alkyl.

8. A compound according to claim 1 having the name; (trans)-1-[N-[[2-[Hydroxy(4-phenylbutyl)phosphinyl]cyclohexyl]carbonyl]-L-alanyl]-L-proline, isomer A, dilithium salt.

9. A compound according to claim 1 having the name; (trans)-1-[N-[[2-[Hydroxy(4-phenylbutyl)phosphinyl]cyclohexyl]carbonyl]-L-alanyl]-L-proline, isomer B, dilithium salt.

10. A compound according to claim 1 having the name; (trans)-1-[N-[[2-[Hydroxy(4-phenylbutyl)phosphinyl]cyclohexyl]carbonyl]-L-alanyl]-L-proline.

* * * * *

UNITED STATES PATENT AND TRADEMARK OFFICE
CERTIFICATE OF CORRECTION

PATENT NO. : 4,849,525
DATED : July 18, 1989
INVENTOR(S) : Weller, et al.

It is certified that error appears in the above-identified patent and that said Letters Patent is hereby corrected as shown below:

Column 5, line 25,  should read

Column 12, line 35, 

Column 14, line 62, "25° L.C." should read -- 25°C. --

Column 18, line 19, "r is an integer from 1 to 4;" should read --R is an integer from 1 to 4; --

Signed and Sealed this

Sixteenth Day of October, 1990

Attest:

HARRY F. MANBECK, JR.

Attesting Officer     Commissioner of Patents and Trademarks